(12) United States Patent
Chase et al.

(10) Patent No.: US 9,226,749 B2
(45) Date of Patent: *Jan. 5, 2016

(54) SKIN STAPLER WITH COMPONENTS OPTIMIZED FOR CONSTRUCTION WITH PLANT BASED MATERIALS

(71) Applicants: Robert N Chase, San Rafael, CA (US); Paul Kardel, Corte Madera, CA (US)

(72) Inventors: Robert N Chase, San Rafael, CA (US); Paul Kardel, Corte Madera, CA (US)

(73) Assignee: NEWGEN SURGICAL, INC, San Rafael, CA (US)

(*) Notice: Subject to any disclaimer, the term of this patent is extended or adjusted under 35 U.S.C. 154(b) by 637 days.

This patent is subject to a terminal disclaimer.

(21) Appl. No.: 13/626,269

(22) Filed: Sep. 25, 2012

(65) Prior Publication Data

US 2014/0084041 A1    Mar. 27, 2014

(51) Int. Cl.
*A61B 17/068* (2006.01)
*A61B 19/02* (2006.01)
*A61B 17/00* (2006.01)

(52) U.S. Cl.
CPC ......... *A61B 17/0684* (2013.01); *A61B 19/0287* (2013.01); *A61B 2017/0023* (2013.01); *A61B 2017/0046* (2013.01)

(58) Field of Classification Search
CPC .. A61B 17/04; A61B 17/1155; A61B 17/104; A61B 17/064

USPC ........... 227/19, 176.1, 177.1; 16/111 R, 430, 16/431, 435, 436

See application file for complete search history.

(56) References Cited

U.S. PATENT DOCUMENTS

| | | | |
|---|---|---|---|
| 4,411,378 A | 10/1983 | Warman | |
| 4,747,531 A * | 5/1988 | Brinkerhoff et al. | 227/19 |
| 4,796,793 A * | 1/1989 | Smith et al. | 227/19 |
| 5,155,878 A * | 10/1992 | Dellis | 16/421 |
| 6,247,204 B1 * | 6/2001 | Hamby et al. | 16/436 |
| 6,796,389 B2 * | 9/2004 | Pusateri et al. | 173/170 |
| 7,703,547 B2 * | 4/2010 | Manacorda et al. | 173/162.2 |
| 7,793,812 B2 | 9/2010 | Moore et al. | |
| 2009/0206137 A1 | 8/2009 | Hall et al. | |

* cited by examiner

*Primary Examiner* — Nathaniel Chukwurah
(74) *Attorney, Agent, or Firm* — Steven A. Nielsen; www.NielsenPatents.com

(57) ABSTRACT

A surgical stapler uses a sheath 1 to protect a handle assembly 80 made of paper pulp products or other eco-friendly material. The sheath includes seams 3 and grip tabs 2 and encloses the handle assembly while the handle assembly is attached to a staple mechanism housing 15. After surgical use or exposure to biohazards, the grip tabs 2 of the sheath may be pulled, uncovering the handle assembly, separating the handle assembly from the staple mechanism housing and allowing the protected handle assembly to be dropped into clean bin container for eco-friendly recycling. The handle assembly and components of the staple mechanism housing are designed to account for the decreased material strength of the recyclable handle assembly. After use, the fouled sheath and staple mechanism housing are disposed in traditional methods.

16 Claims, 21 Drawing Sheets

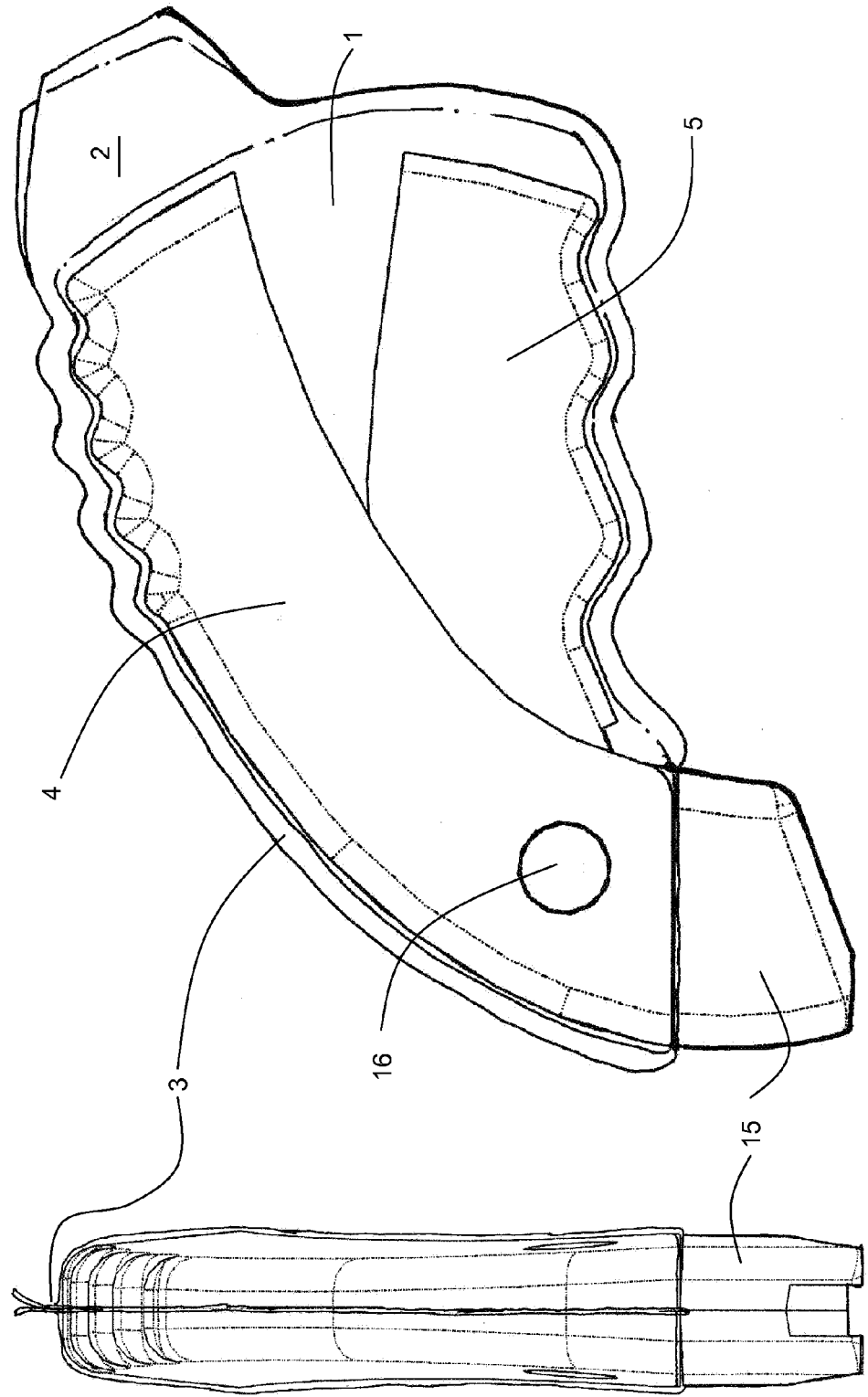
FIG. 1 FRONT VIEW
FIG. 2 SIDE VIEW

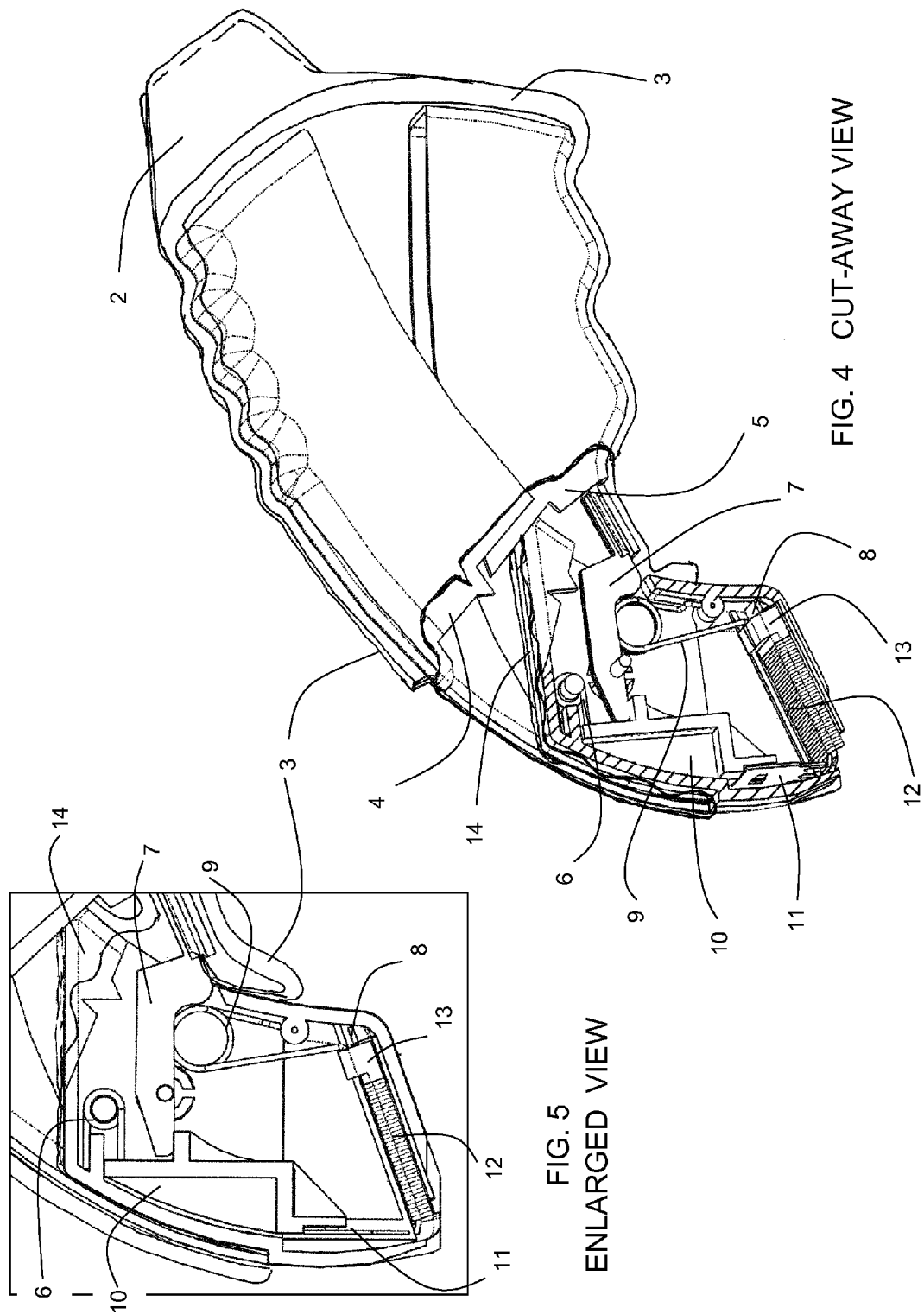

CUTAWAY VIEW
WITHOUT SHEATH

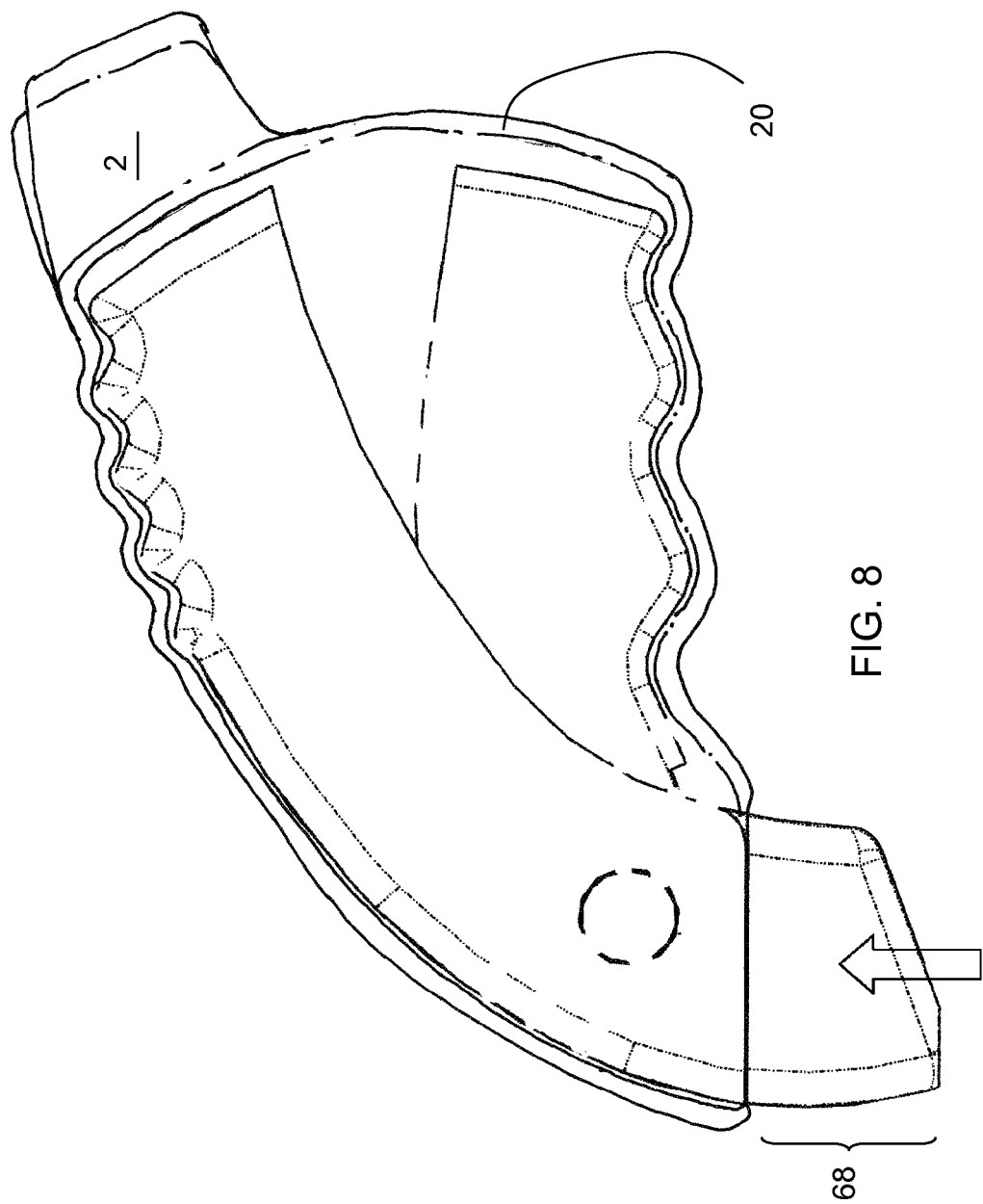

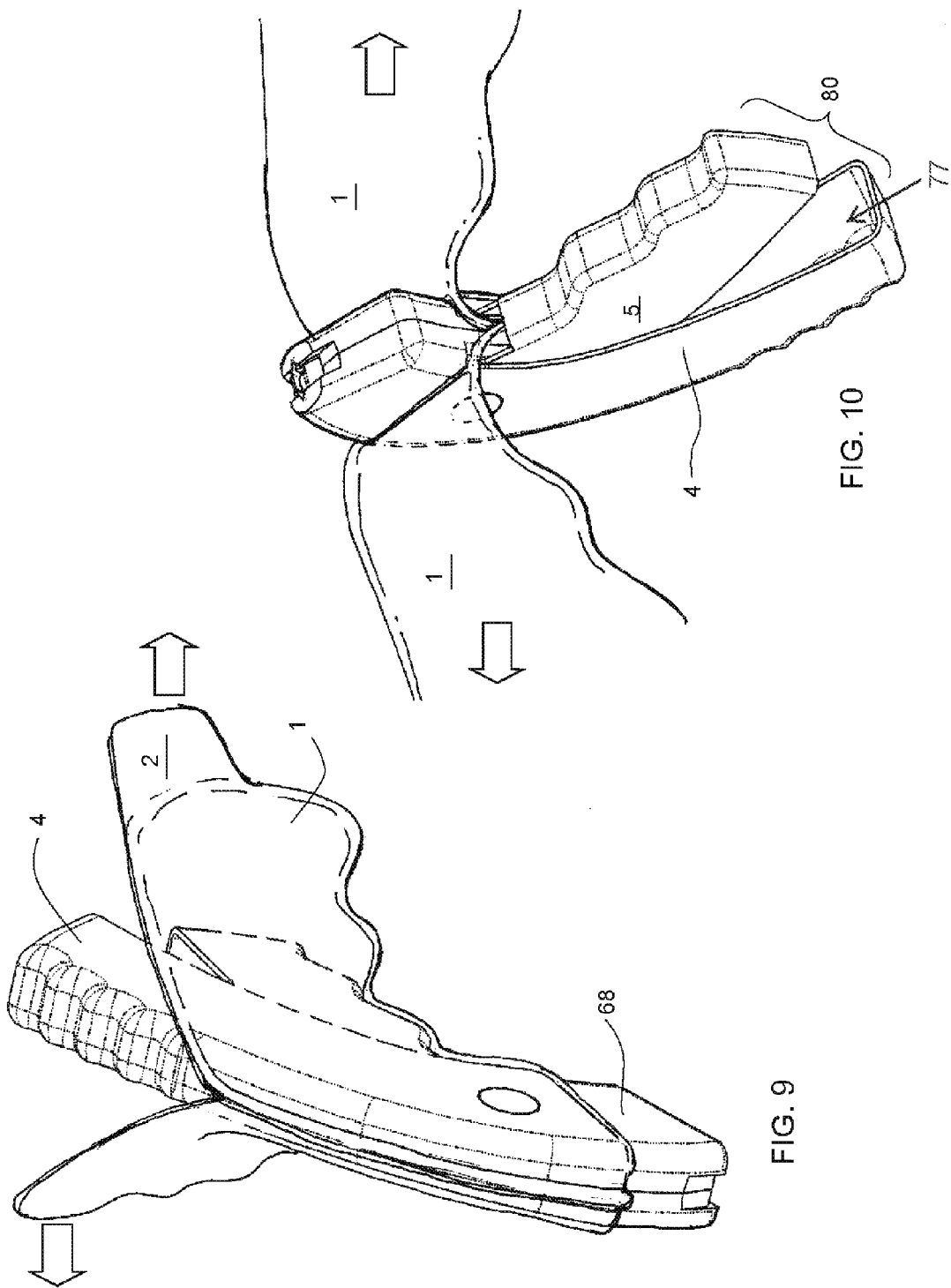

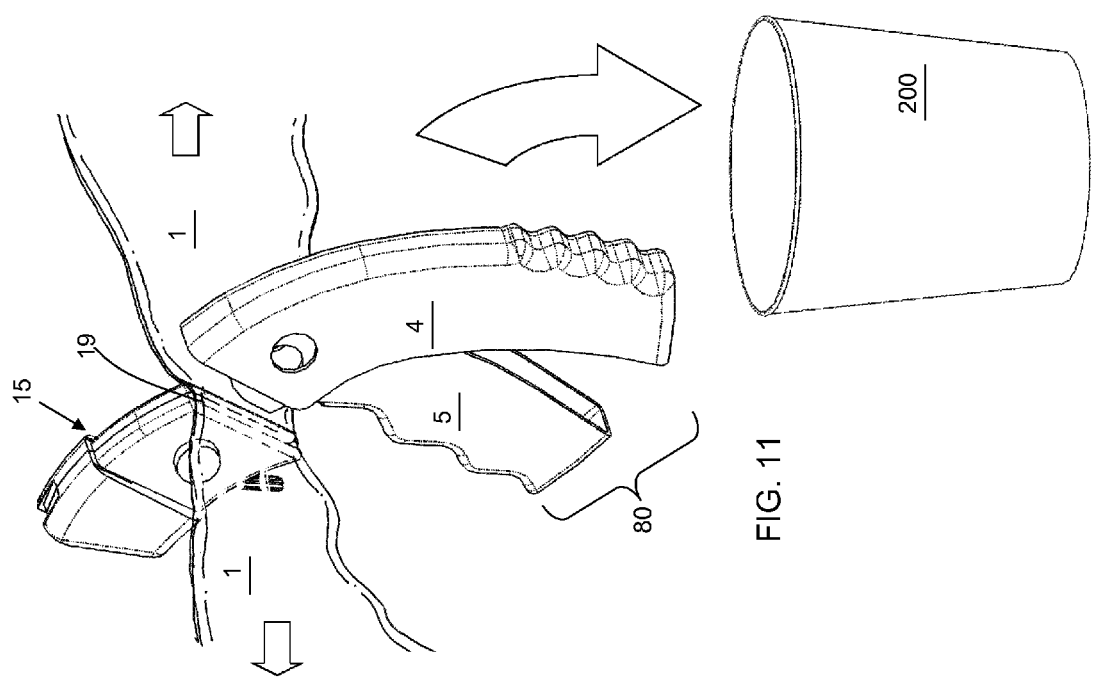

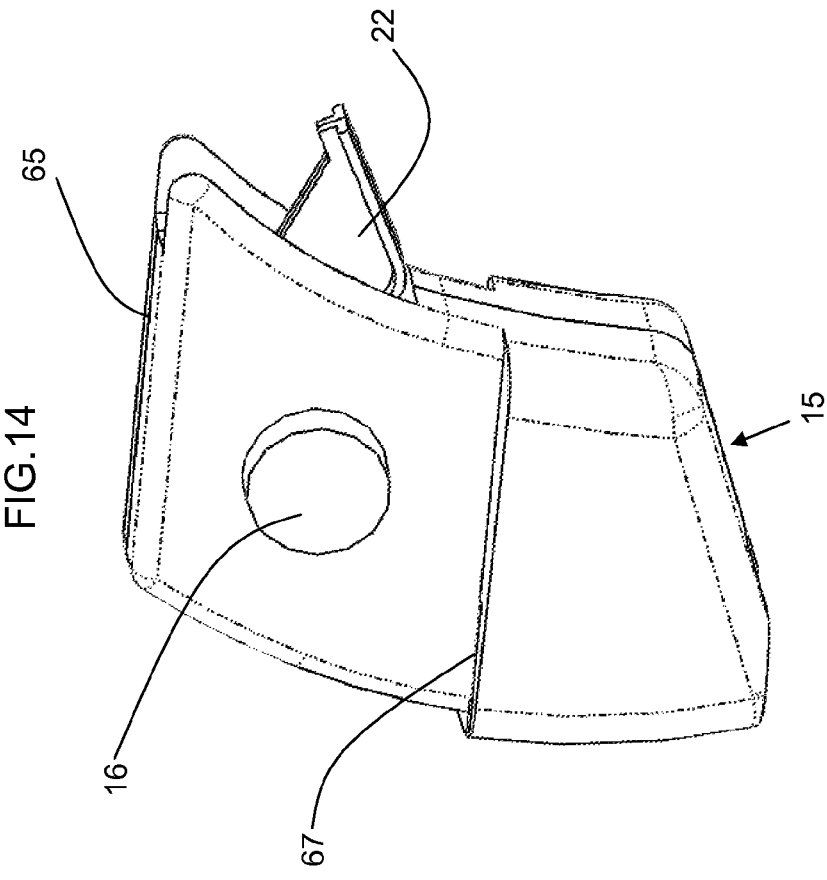
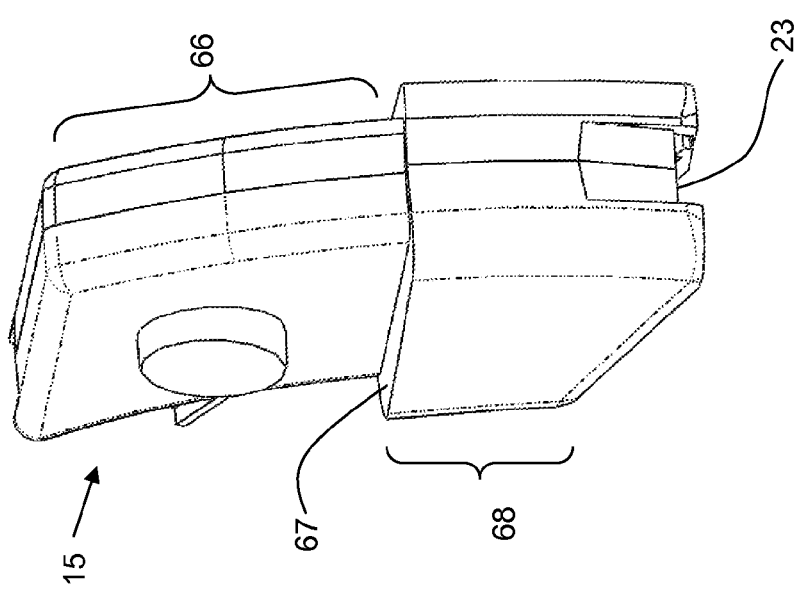
STAPLER MECHANISM ASSEMBLY

STAPLER HOUSING
DETAIL VIEW

ACTUATOR LEVER
DETAIL VIEW

STAPLE FOLDER BLOCK DETAIL VIEW

STAPLE ADVANCE SPRING DETAIL VIEW

RETURN SPRING DETAIL VIEW

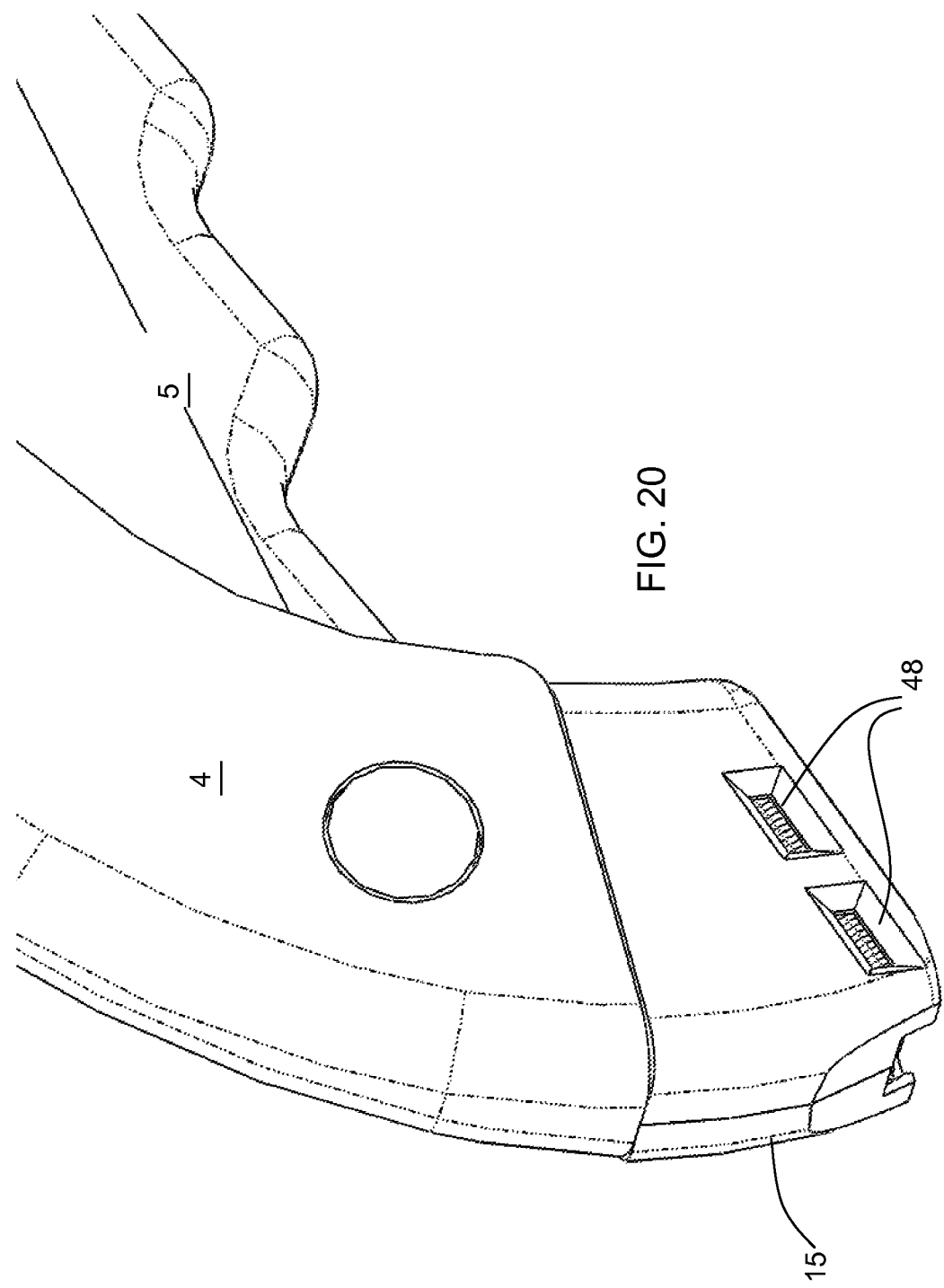

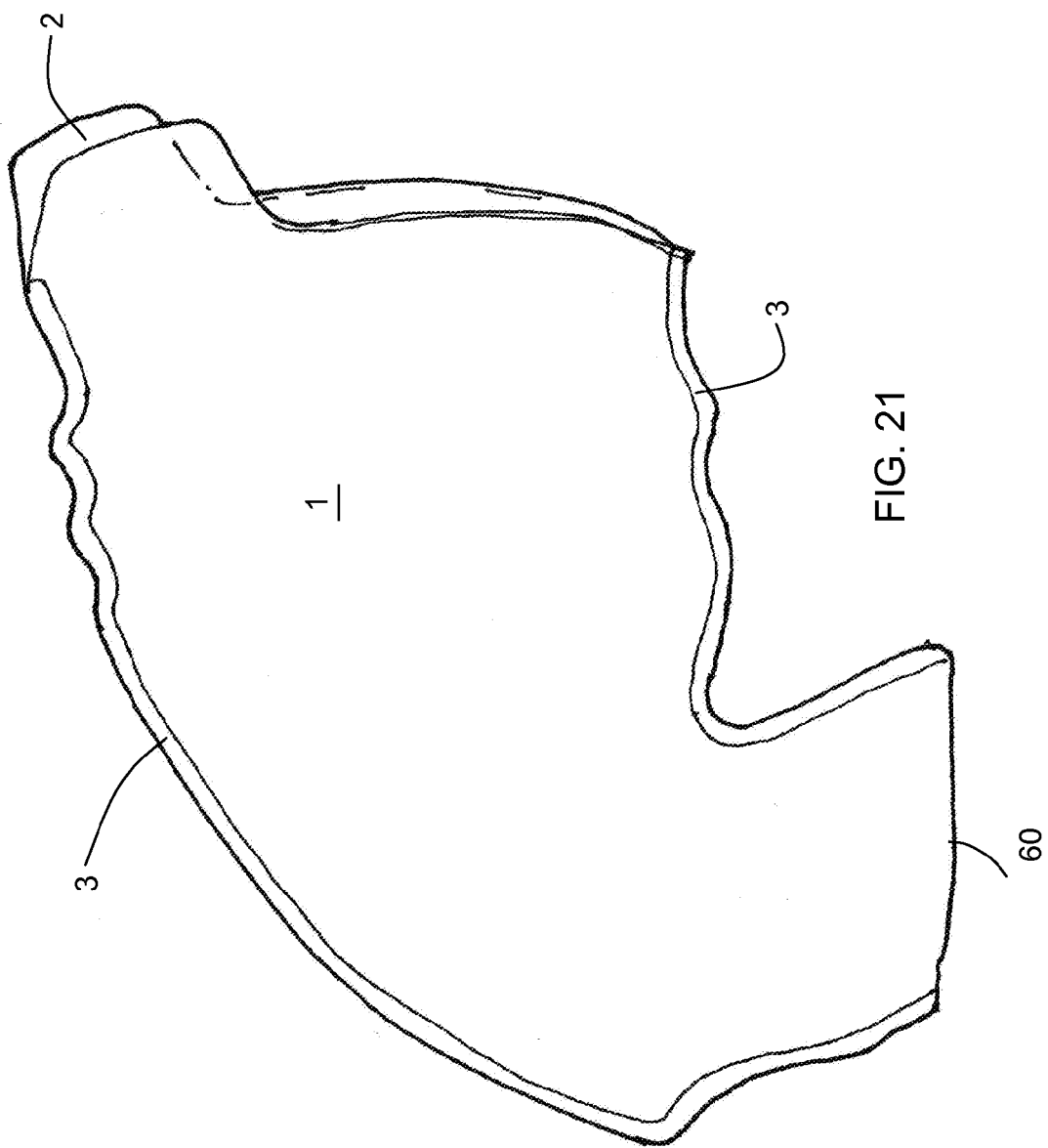

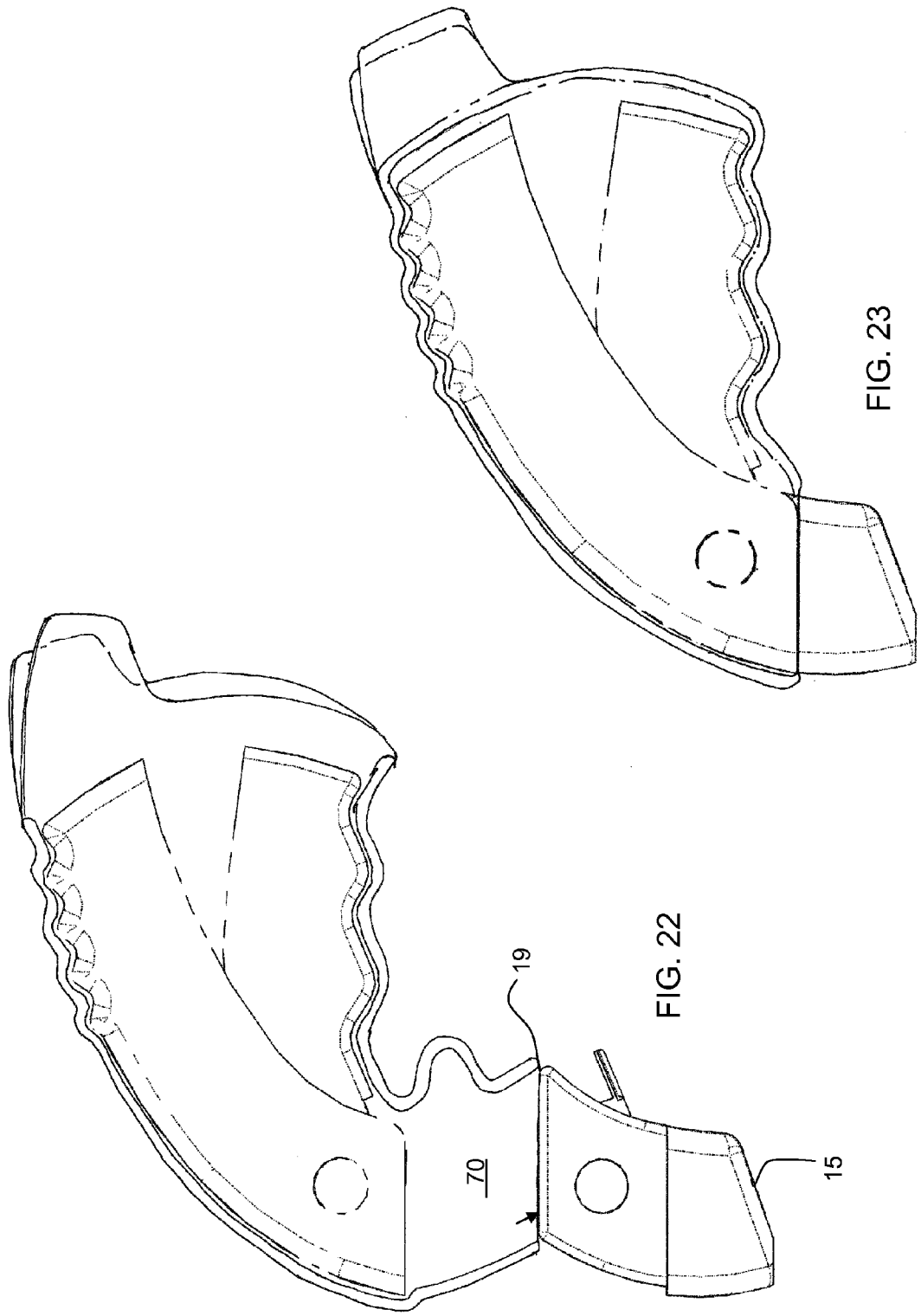

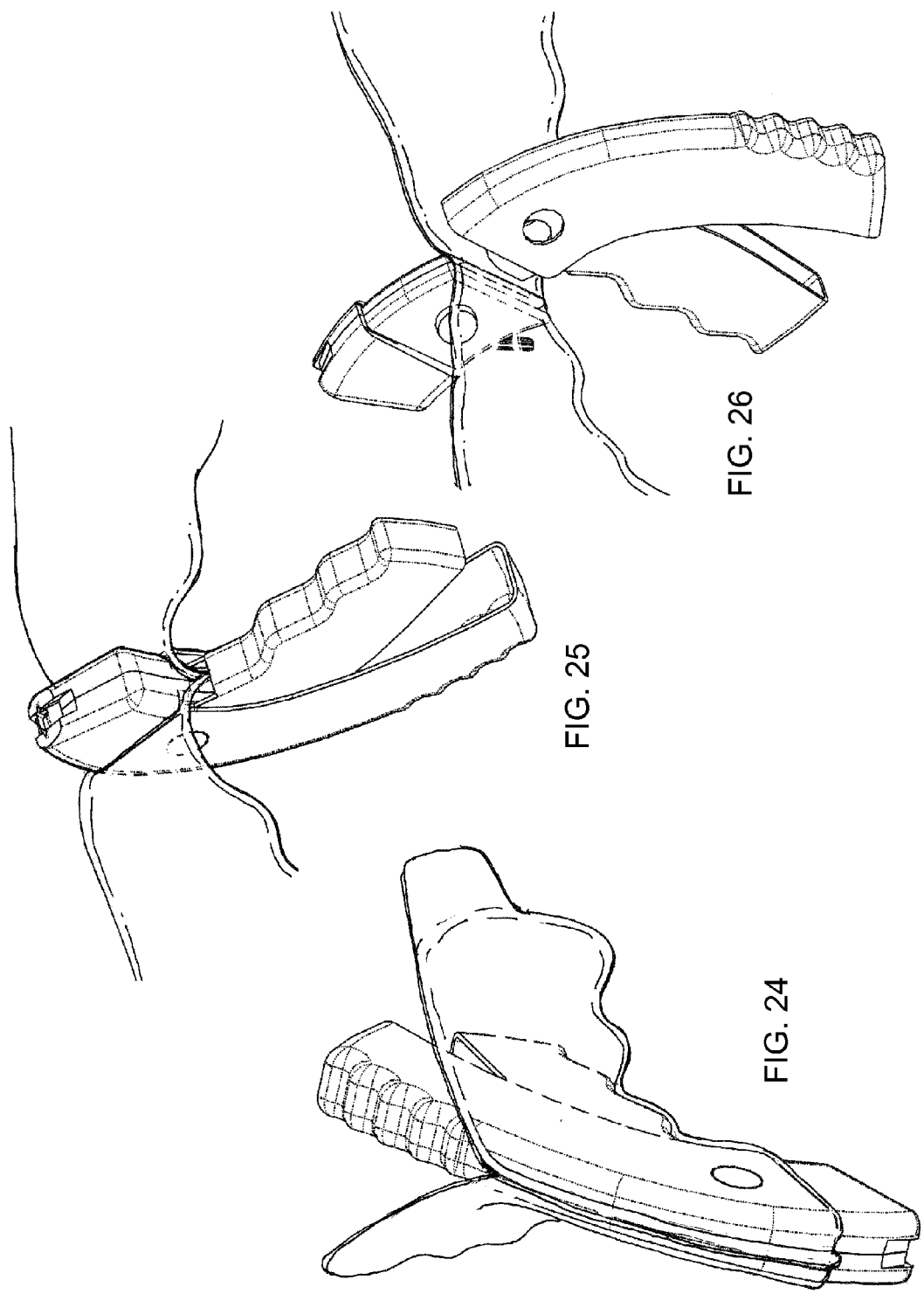

SKIN STAPLER WITH COMPONENTS OPTIMIZED FOR CONSTRUCTION WITH PLANT BASED MATERIALS

CROSS-REFERENCE TO RELATED APPLICATIONS

N/A

BACKGROUND OF THE INVENTION (1) Field of the Invention

The invention generally relates to disposable skin staplers. More particularly, the invention relates to means and methods of maximizing the volume of clean eco-friendly recyclable parts while minimizing the volume of biohazard material created after use.

(2) Description of the Related Art

Other disposable skin staplers are known in the related art. For example, U.S. Pat. No. 4,411,378 issued on Oct. 25, 1983 to Warman discloses the use of plastics in making a skin stapler. The use of plastics purportedly makes the Warman stapler disposable. After one use, the entire Warman stapler becomes a biohazard waste product to be disposed of by incineration.

U.S. Published Patent Application 2009/0206137 by Hall et al, published on Aug. 20, 2009 discloses a disposable loading unit for inserting staples into a traditional stapler. While the addition of staples to a stapler may prolong the useful life of a stapler, the stapler contemplated by Hall appears to be devoid of any recyclable components and appears to undergo traditional sterilization procedures before each use.

U.S. Pat. No. 7,793,812 issued on Sep. 14, 2010 to Moore et al discloses a motor driven disposable loading unit for adding staples into a traditional stapler. Here again, no means or methods are even contemplated to recycle parts of the stapler in an environmentally sustainable manner.

BRIEF SUMMARY OF THE INVENTION

The present invention overcomes shortfalls in the related art by presenting an unobvious and unique combination and configuration of methods and components that prevent biohazard fouling of various stapler components. Embodiments of the present invention protect a handle and actuator grip from contamination and provide an integrated sheathing system to eject clean parts into a common recycling container intended for typical consumer paper products. After use, the disclosed handle assembly parts may be mixed with other consumer paper products for recycling. During use of a disclosed stapler, a protective sheathing keeps blood and other material away from the disclosed handle assembly. The disclosed handle assembly is artfully made from wood pulp products or other eco-friendly materials and hence is well suited for clean bin recycling. The construction of the disclosed handle assembly overcomes shortfalls in the related art wherein hard plastics have been used to achieve the necessary material strength.

After surgical use, tabs upon the disclosed sheath system are pulled, removing the sheathing from the handle assembly and ejecting the handle assembly into a recycling container, for clean-bin recycling.

The sheathing and sheathing tabs remain in the hands of the user. The sheathing remains attached to a staple mechanism housing. The user then drops the sheathing and attached staple mechanism housing into a biohazard container. Thus, the present invention overcomes shortfalls in the art by significantly reducing the volume of stapler components destined for a biohazard container.

In the known related art, entire stapling systems are subjected to biohazard exposure requiring entire systems to be incinerated, increasing pollution and the consumption of materials. In the prior art, the term "disposable" relates to the use of plastics that are inexpensive to produce. Unfortunately, the prior art fails to consider the elements of sustainability in the production and disposal of surgical staple systems.

Typically in a surgical environment, tools coming into direct contact with a patient are considered a biohazard and require 1.) expensive sterilization, a labor intensive process using copious amounts of hot water and cleaning chemicals or 2.) costly incineration, burning fuel and emitting harmful particulates into the air. The trend in the art is to use plastics to create one time use staplers and to incinerate such staplers after use. Thus, the prior art teaches away from the present embodiments and methods.

The prior art fails to teach, suggest or contemplate the disclosed use of sheathing material to protect stapler components or the construction of stapler components using wood pulp products. Disclosed embodiments present an unobvious integration of a sheathing material sealed onto and intertwined with stapler components.

Embodiments of the invention overcome shortfalls in the art by the careful engineering of protected components such that disclosed handles and actuator grips may be made from Molded Pulp Fiber (MPF) or other wood pulp products. The designs of the related art require the use of hard plastics to achieve the needed material strength for proper staple operation. The disclosed stapler mechanism designs overcome such prior art shortfalls.

The disclosed embodiments do not present a hardship or handicap to medical personal. The integrated sheathing system presents two tear tabs, that when pulled apart, eject the underlying and clean wood pulp components into clean bin recycle containers.

The disclosed embodiments include new staple mechanism housings, handle assemblies and other related components that require less force upon the disclosed handles and actuator grips, allowing for such components to be made of eco-friendly materials.

These and other objects and advantages will be made apparent when considering the following detailed specification when taken in conjunction with the drawings.

BRIEF DESCRIPTION OF THE DRAWINGS

FIG. 1 depicts a front view of a disclosed surgical stapler

FIG. 2 depicts a side view of a disclosed surgical stapler

FIG. 4 depicts a side view and cutaway view of a disclosed surgical stapler

FIG. 5 depicts an expanded view of various stapler components

FIG. 8 depicts a disclosed surgical stapler in a state of near assembly FIG. 9 depicts a sheath being separated from a handle assembly FIG. 10 depicts a sheath in a further state of separation FIG. 11 depicts a handle and actuator grip level being separated from a staple mechanism housing FIG. 13 depicts a front perspective view of a staple mechanism housing FIG. 14 depicts a side view of a staple mechanism housing FIG. 20 depicts a perspective view an disclosed surgical stapler having a void area for viewing remaining staples FIG. 21 depicts a disclosed sheath FIG. 22 depicts a staple mechanism housing in connection with a sheath FIG. 23 depicts an assembled surgical stapler with sheath attached FIGS. 24 to 26 depict a disassembly procedure of a surgical stapler

Figure 3:
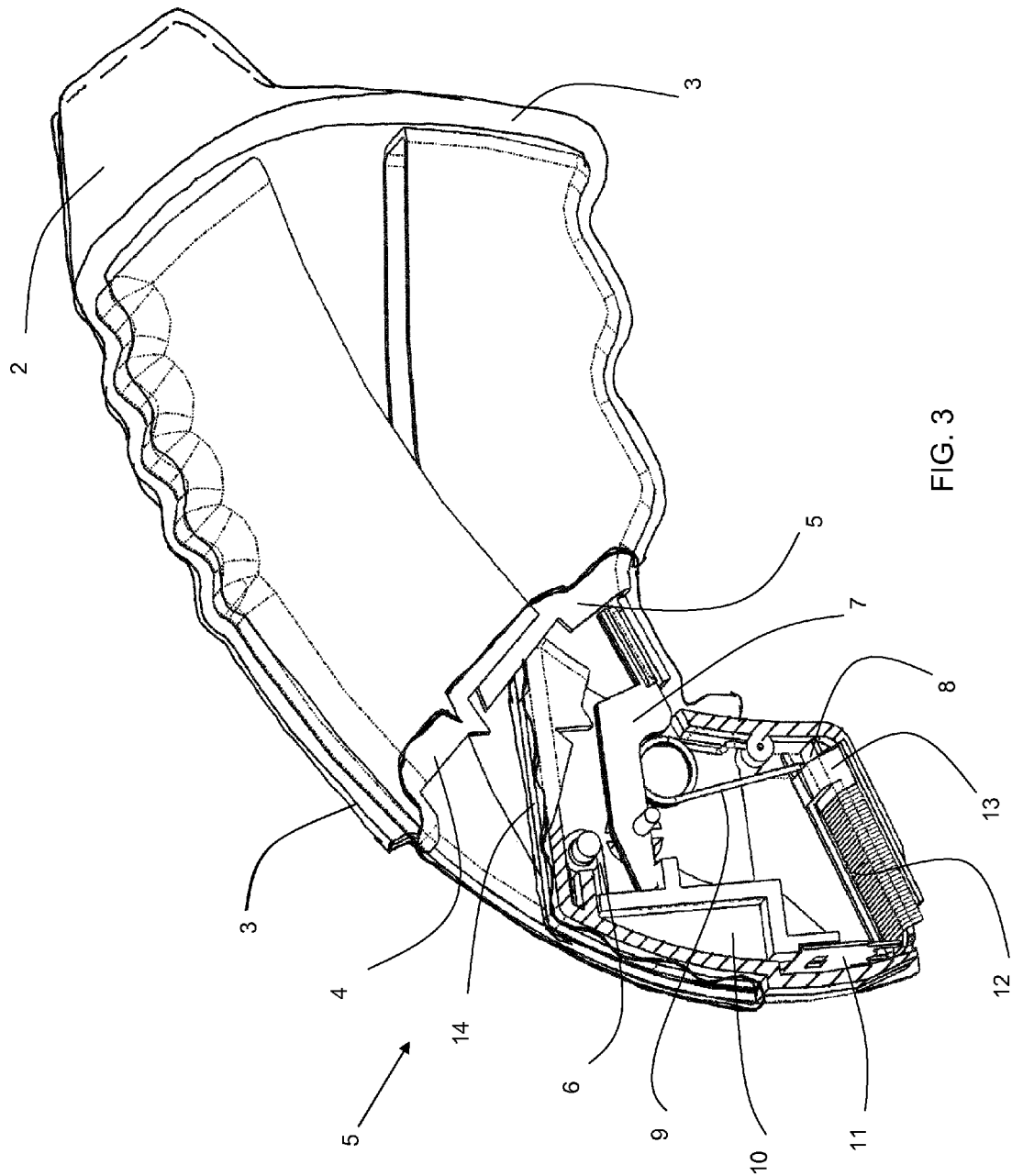
FIG. 3 depicts a side view and cutaway view of a disclosed surgical stapler

REFERENCE NUMERALS IN THE DRAWINGS 1 sheath
2 grip tabs attached to the sheath 1, used to open sheath at proximal side
3 seam on sheath, seam tears apart as part of disposal process
4 handle, accepts actuator grip 5 and staple mechanism housing
5 actuator grip lever, sometimes made of Molded Pulp Fiber or MPF
6 return spring or staple folder
7 actuator lever, sometimes made of molded plastic
8 staple carrier tray, sometimes made from a stamped stainless steel sheet
9 staple advance spring, sometimes made of stainless steel wire
10 staple folder block, sometimes made of molded plastic
11 staple folder plate, sometimes made of stamped stainless steel
12 staple stack, comprised of a plurality of staples
13 staple advance block, sometimes made of molded plastic
14 section of sheath folded inside handle and actuator grip lever
15 staple mechanism housing, comprised of a right 15R side and left side 15L, sometimes made of molded plastic
15R right side of staple mechanism housing 15
15L left side of staple mechanism housing 15
16 handle pivot boss, mates with round void 75 of handle and void 76 of actuator grip
17 sheath with sides sealed and back open for handle insertion
19 attachment between sheath and stapler mechanism assembly which may be accomplished with various means such as adhesive bonding, ultrasonic welding or mechanical fastening
20 sheath in a final seal configuration after staple mechanism housing 15 is inserted into a handle assembly 80
22 distal section of actuator lever arm, extends from staple mechanism housing and is rotated by a pivoting actuator grip handle to fold staples
23 recessed view area of staple mechanism housing 15, allowing a surgeon a clear view of the stapling process and clearance for everted tissue to be stapled
24 boss of staple mechanism housing 15, used with return spring 6
25 curved rib of staple mechanism housing 15, used to center staple advance spring 9 within staple mechanism housing 15
26 pivot void found within staple mechanism housing 15 positioned to allow the staple advance spring 9 to clear all internal parts and to apply even pressure throughout travel
27 recess within staple mechanism housing 15, for staple carrier tray 8, used to properly position staples
28 track within staple mechanism housing 15, used for staple folder plate 11
29 front inside wall of staple mechanism housing 15, used to retain a staple during forming without allowing staples to jam due to multiple staple feed
30 vertical track within staple mechanism housing 15, used for staple folder block 10
31 pivot void found within staple mechanism housing 15, used for actuator lever 7
32 rib of actuator lever 7, contoured to clear other internal components throughout movement
33 pivot pin of actuator lever, rotates in the pivot void 31 of the staple mechanism housing 15
34 block contact area of actuator lever 7, used for a smooth interface with staple folder block 10
35 wide rib of actuator lever 7, provides rigidity to actuator lever and distributes actuating force from actuator grip lever 5
36 vertical rib of staple folder block 10, runs in vertical track 30 of staple mechanism housing 15
37 protruding surface of staple folder block 10, mates with actuator lever 7
38 ribs or curved ribs of staple folder block 10, used for more even transfer of forces to staple folder plate 11
39 recessed area of staple folder block 10, used for staple folder plate 11
40 raised block of staple folder block 10, mates with void within staple folder plate 11
41 pivot leg of staple advance spring 9, mates with void of staple mechanism housing 15
42 offset of staple advance spring 9, centers the staple advance spring 9 within the staple mechanism housing 15
43 triple loop of staple advance spring 9, retains the staple advance spring 9 within limits of intended elasticity
44 pusher leg of staple advance spring 9, rotates around triple loop 43 to advance staples
45 leg of staple advance spring 9, mates with staple advance block 13
46 double loop of return spring 6, keeps the return spring 6 within limits of intended elasticity
47 legs of return spring 6, urge a staple folder block 10 to a starting position
48 voids within in staple mechanism housing 15, used to view the remaining quantity of staples
50 void within staple folder plate 11, used to mate with staple folder block
60 folded edge of sheath 1

65 superior side of staple mechanism housing 15, the superior side used as an attachment point 19 for the folded edge 60 of a sheath 66 narrow section of staple mechanism housing 15, fits into inferior openings within the handle assembly 80

67 lateral ledge of staple housing mechanism 15

68 base section of staple mechanism housing 15

70 loose section of sheath 1 for placement within handle assembly 80

75 center void within handle 4, used to mate with boss 16

76 center void within actuator grip lever, used to mate with boss 21

77 interior void within handle 4, the interior void defined by a plurality of exterior handle walls 80 handle assembly, comprising a handle 4 and actuator grip lever 5

100 a disclosed surgical stapler in general 200 clean waste recycle bin

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines.

FIG. 1 depicts a front view with a stapler mechanism housing 15 and a seal seam 3.

FIG. 2 depicts a side view of a stapler having a handle 4, sometimes made of molded Pulp Fiber (MPF) or other wood pulp product, a handle pivot boss 16, a sheath 1, with the sheath having a pair of grip tabs 3.

FIG. 3 depicts a sectional view showing sheath tab 2, various sections of seal seams 3 as well various components within the staple mechanism housing 15. The staple mechanism housing includes a staple stack 12, a staple advance block 13, a staple carrier tray 8, an actuator lever 7, a return spring 6, a staple advance spring 9, a staple folder plate 11, and a stapler folder block 10.

FIG. 4 depicts a sectional view as in FIG. 3 and is used as a reference for FIG. 5. FIG. 5 depicts views of a return spring 6, an actuator lever 7, a staple carrier tray 8, a staple advance spring 9, a staple folder block 10, a staple folder plate 11, a staple stack 12 or stack of staples, a staple advance block 13, and a sheath section 14 folded inside a handle 4.

Figure 6:
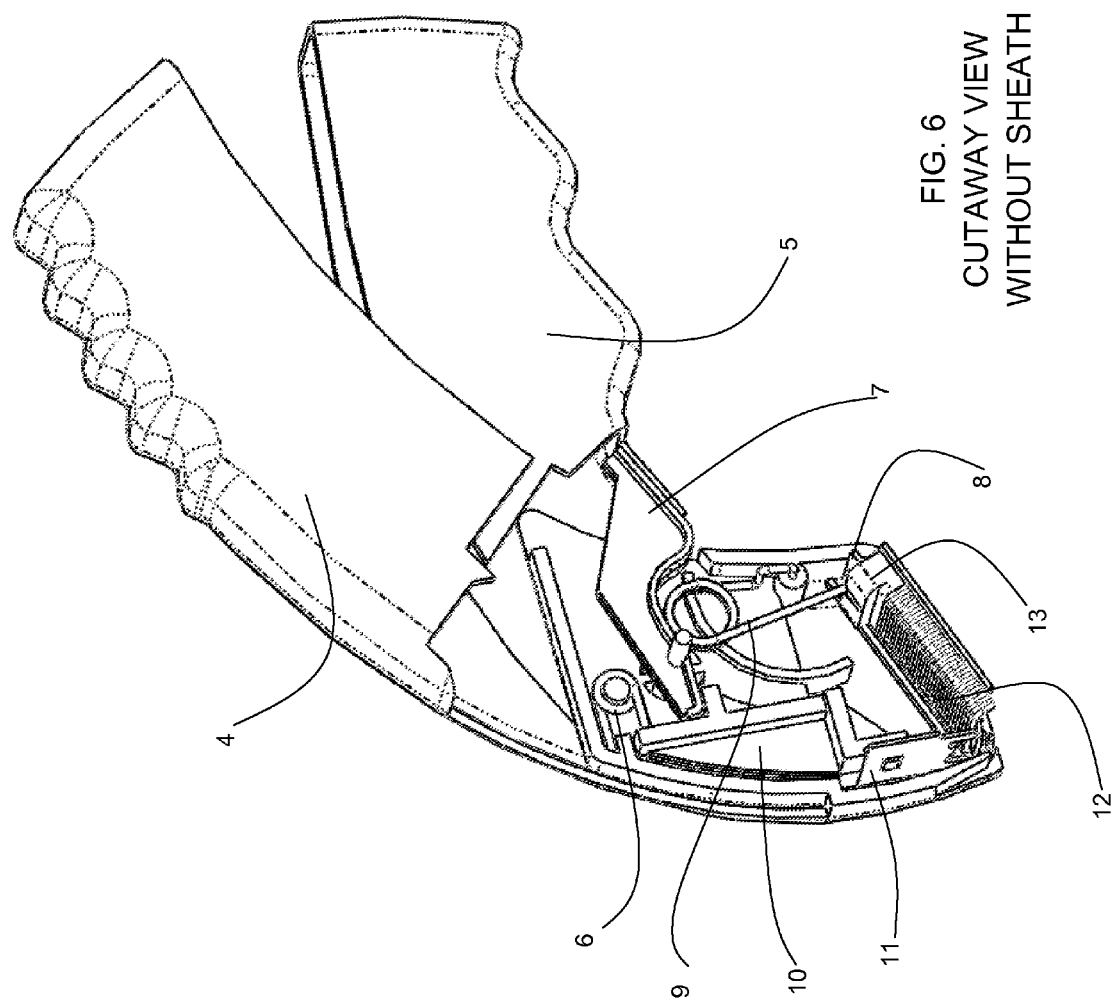
FIG. 6 depicts a sectional view of a disclosed surgical stapler without a sheath

FIG. 6 depicts an embodiment before a sheath is applied and shows a handle 4 superior to an actuator grip lever. FIG. 6 further depicts a return spring 6, an actuator lever 7, a staple carrier tray 8, a staple advance spring 9, a staple folder block 10, a staple folder plate 11, a staple stack 12 or stack of staples and a staple advance block 13.

Figure 7:
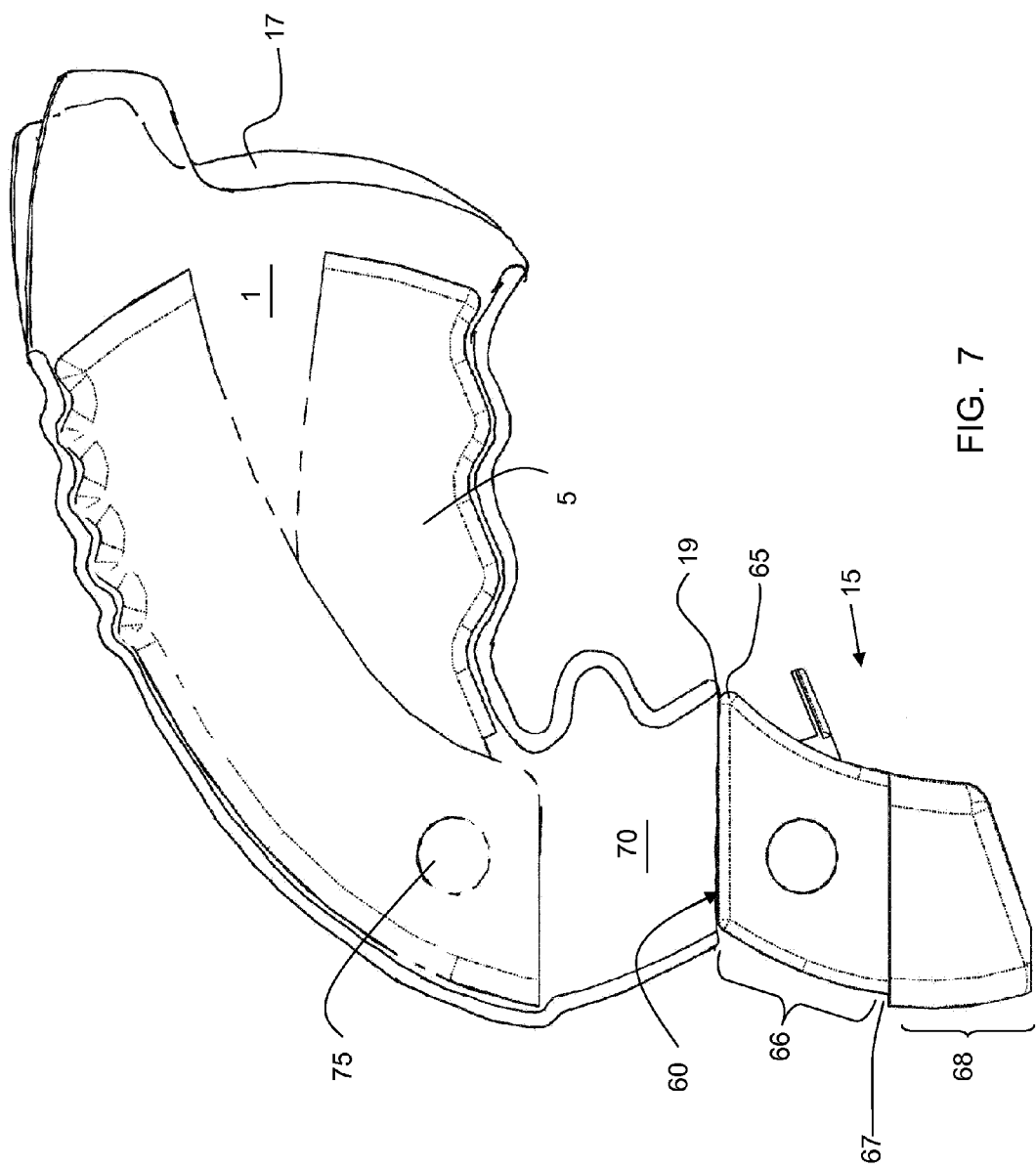
FIG. 7 depicts a disclosed surgical stapler in a state of partial assembly

FIG. 7 depicts a sheath 1 with sides sealed with an open back section 17. When the sheath is in an open position 17, a handle and actuator grip may be inserted into the sheath. A folded edge 60 of the sheath is shown in attachment 19 with the superior side 65 of a staple mechanism housing 15.

In FIG. 7, the sheath includes a loose section 70 which folds over a narrow section 66 of the staple mechanism housing during the insertion process.

FIG. 8 depicts a staple mechanism housing inserted into a handle assembly. The sheath protrudes from the void 75 of the handle and the sheath covers the boss of the staple mechanism housing. A base section 68 of the staple mechanism housing is left exposed. The sheath is shown in a condition 20 wherein the sheath is in a final seal configuration after the staple mechanism housing is inserted into the handle assembly.

FIG. 9 depicts a sheath with tabs 2 being pulled outwardly, and exposing the handle 4.

FIG. 10 depicts a sheath that is flexed at or near a lateral ledge of staple mechanism housing. The sheath is shown to have cleared the handle assembly 80. The pulling of the sheath is just starting to separate the handle assembly from the staple mechanism housing.

FIG. 11 depicts a separated handle 4 and actuator grip lever 4 falling into a clean waste recycle bin 200. The sheath 1 is shown secured at an attachment point 19 or attachment line found upon a superior side of the staple mechanism housing.

Figure 12:
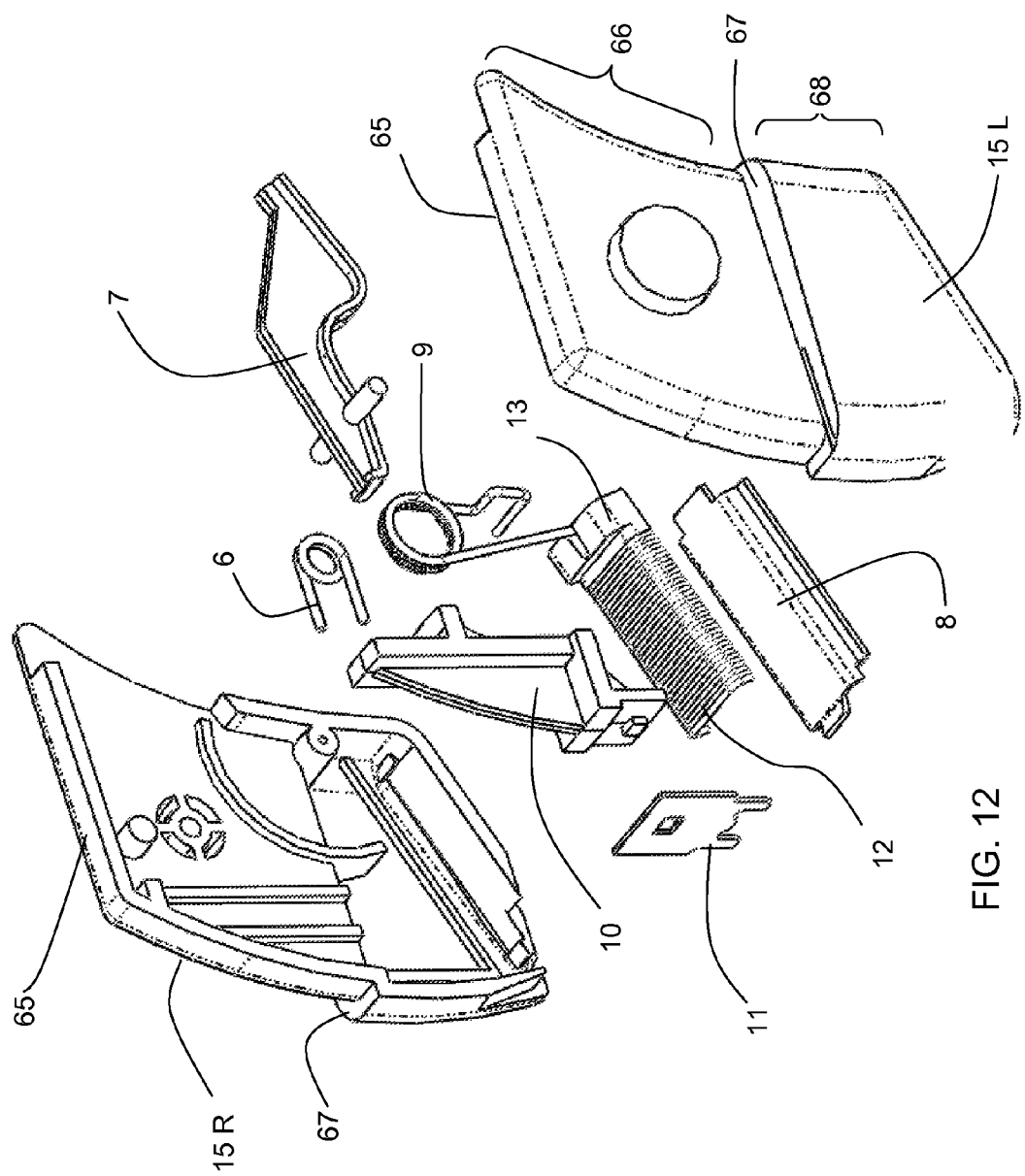
FIG. 12 depicts an exploded view of a staple mechanism housing

FIG. 12 depicts an exploded view of a staple mechanism housing comprising a right side 15R, left side 15L, a return spring 6, actuator lever 7, staple carrier tray 8, staple advance spring 9, staple folder block 10, staple folder plate 11, a staple stack 12 and a staple advance block 13. The left side 15 L of the staple mechanism housing is shown with a superior side 65 which is sometimes used as a point or line of attachment 19 to secure a sheath. A narrow section 66 is found upon a superior end of the left side 15L component, the narrow section fits into an end of the handle assembly. A lateral ledge 67 stops the staple mechanism housing from further insertion into the handle assembly.

FIG. 13 depicts an assembled staple mechanism housing 15 having a narrow section 66, three lateral ledges 67, a base section 68 and a recessed view area sometimes used by an end user for clear view of the stapling process and for clearance of everted tissue to be stapled.

FIG. 14 depicts a side view of a an assembled staple mechanism housing 15 having a handle pivot boss 16, superior side 65, three lateral ledges 67 and a distal section 22 of actuator lever arm, extends from staple mechanism housing and is rotated by a pivoting actuator grip handle to fold staples.

Figure 15:
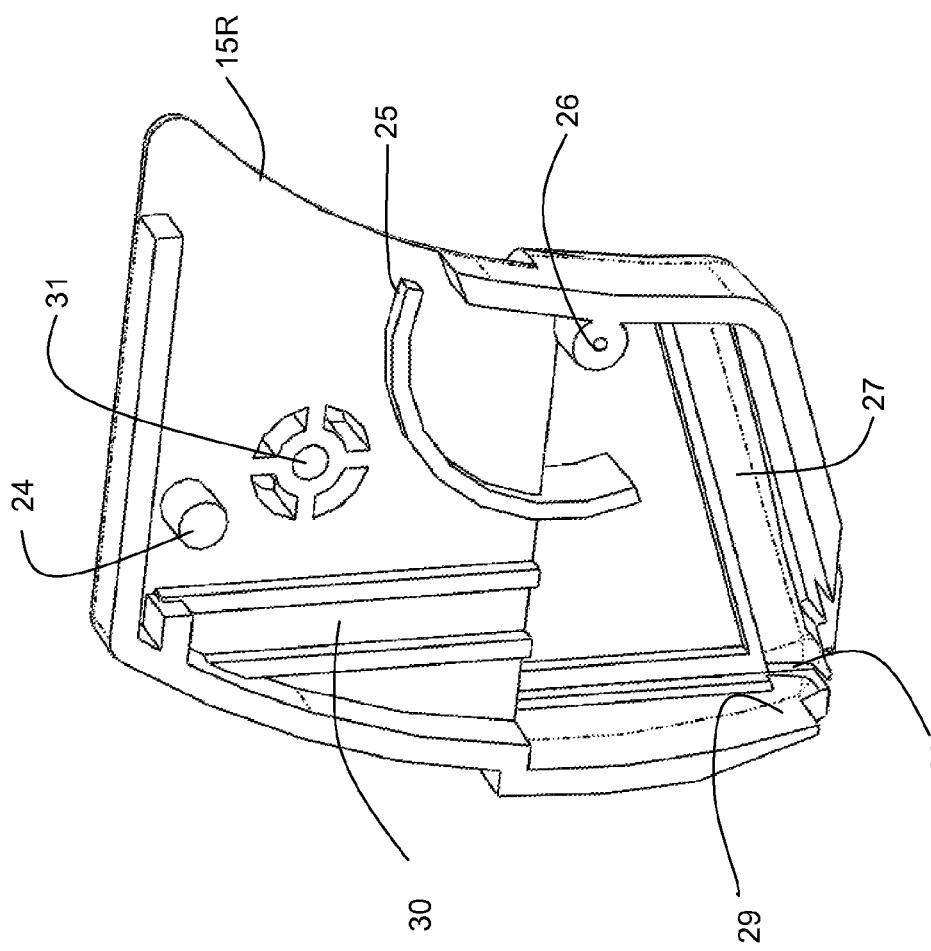
FIG. 15 depicts a sectional view of a staple mechanism housing

FIG. 15 depicts a right side 15R of a staple mechanism housing comprising a boss 24 used with a return spring 6, a curved rib 25 used to center staple advance spring 9 within a staple mechanism housing, a pivot void 26 positioned to allow the staple advance spring 9 to clear all internal parts and to apply even pressure throughout travel of the actuator lever 7. FIG. 15 also depicts a recess 27 for use with a staple carrier tray 8, used to properly position staples. A track 28 is used to guide a staple folder plate 11. A front inside wall 29 may be used to retain a staple during forming without allowing staples to jam due to multiple staple feed. A vertical track 30 is sometimes used with a staple folder block 10. A pivot void 31 is defined by a vertical wall of staple mechanism housing, the pivot void sometimes used by a actuator lever 7.

Figure 16:
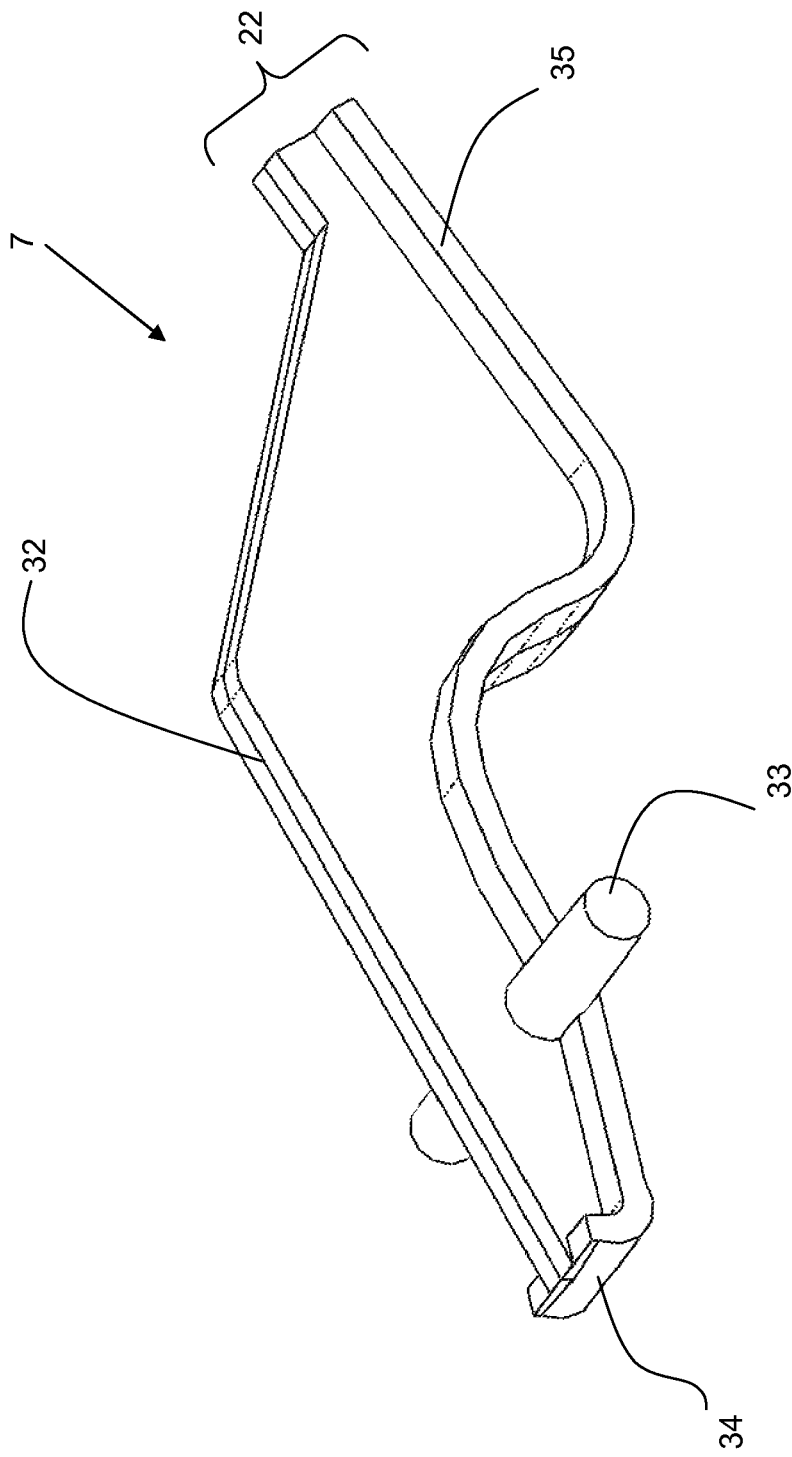
FIG. 16 depicts a perspective view of a actuator lever

FIG. 16 depicts an expanded view of an actuator lever 7 having one or more ribs 32, the ribs contoured to avoid contact with other components within a staple mechanism housing. An actuator lever 7 may have one or more pivot pins 33, sometimes used to rotate within a pivot void 31 of a staple housing mechanism. A block contact area 34 is sometimes used as a contact area or interface with staple folder block 10. The curved design of the block contact area provides a smooth interface and operation with a staple folder block. A wide rib 35 provides rigidity to the actuator lever and distributes actuating force from the actuator grip lever 5. A distal section 22 of the actuator lever may extend from staple mechanism housing and is rotated by a pivoting the actuator grip handle to fold staples.

Figure 17:
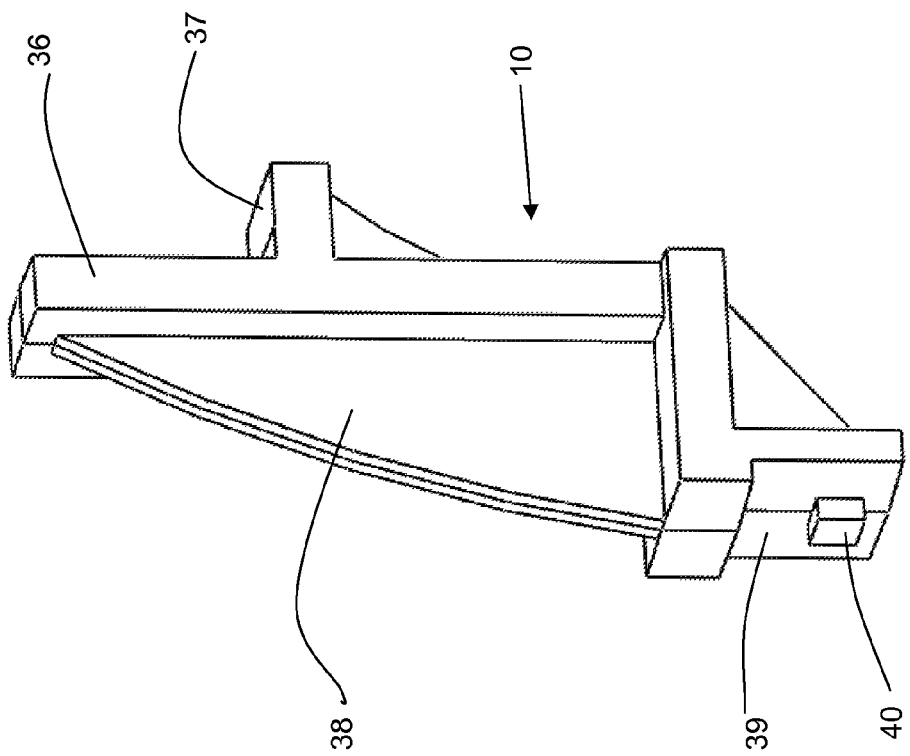
FIG. 17 depicts a perspective view of a staple folder block

FIG. 17 depicts an expanded view of a staple folder block 10 having a protruding surface 37 sometimes used to contact an actuator lever 7. A vertical rib 36 may be fitted or run in a vertical track 30 of the staple mechanism housing 15. A staple folder block may have one or more ribs 38, sometimes used to evenly distribute force to a staple folder plate 11. A recessed area 39 of the staple folder block 10 is sometimes used with a staple folder plate. The recessed area may have a raised block 40 sometimes used in connection with a void within a staple folder plate 11.

Figure 18:
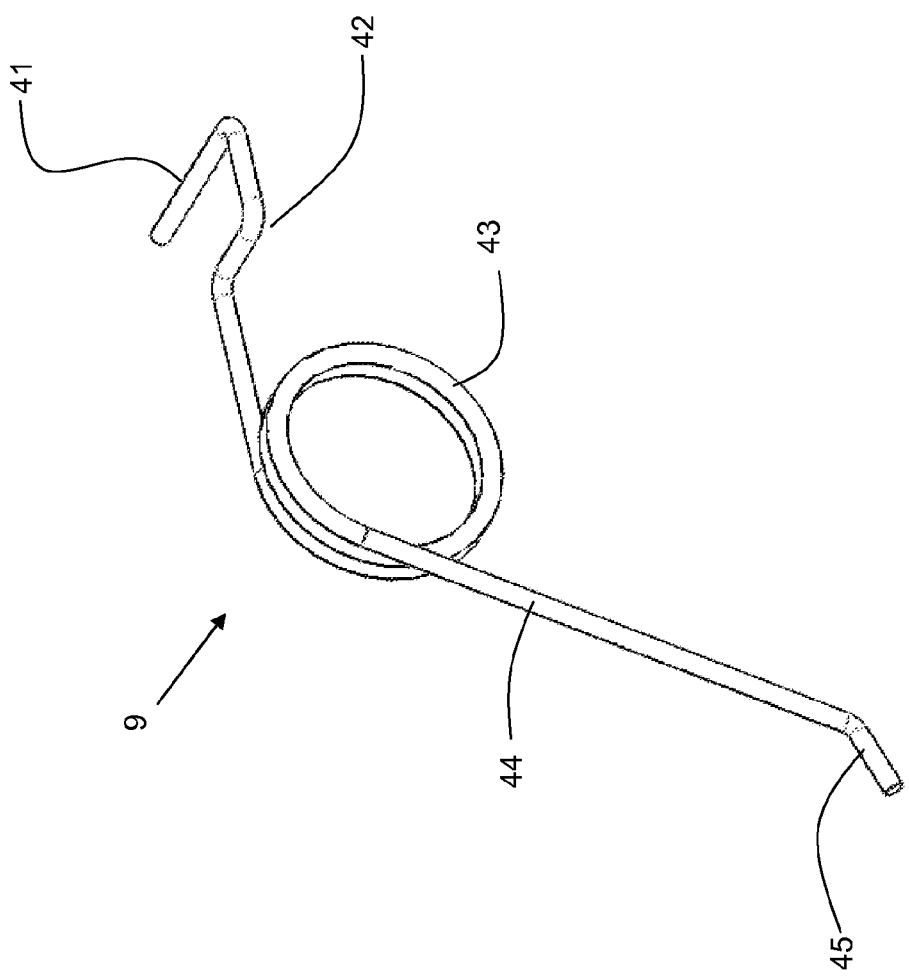
FIG. 18 depicts a perspective view of a staple advance spring

FIG. 18 depicts a staple advance spring 9 having a pivot leg 41 sometimes being inserted into a void within staple mechanism housing. An offset 42 centers the staple advance spring within the staple mechanism housing 15. The staple advance spring has a triple loop 43 which assists in keeping the spring within intended limits of elasticity. A pusher leg 44 flexes around the triple loop to advance staples. A leg 45 of the staple advance spring mates with a staple advance block 13.

Figure 19:
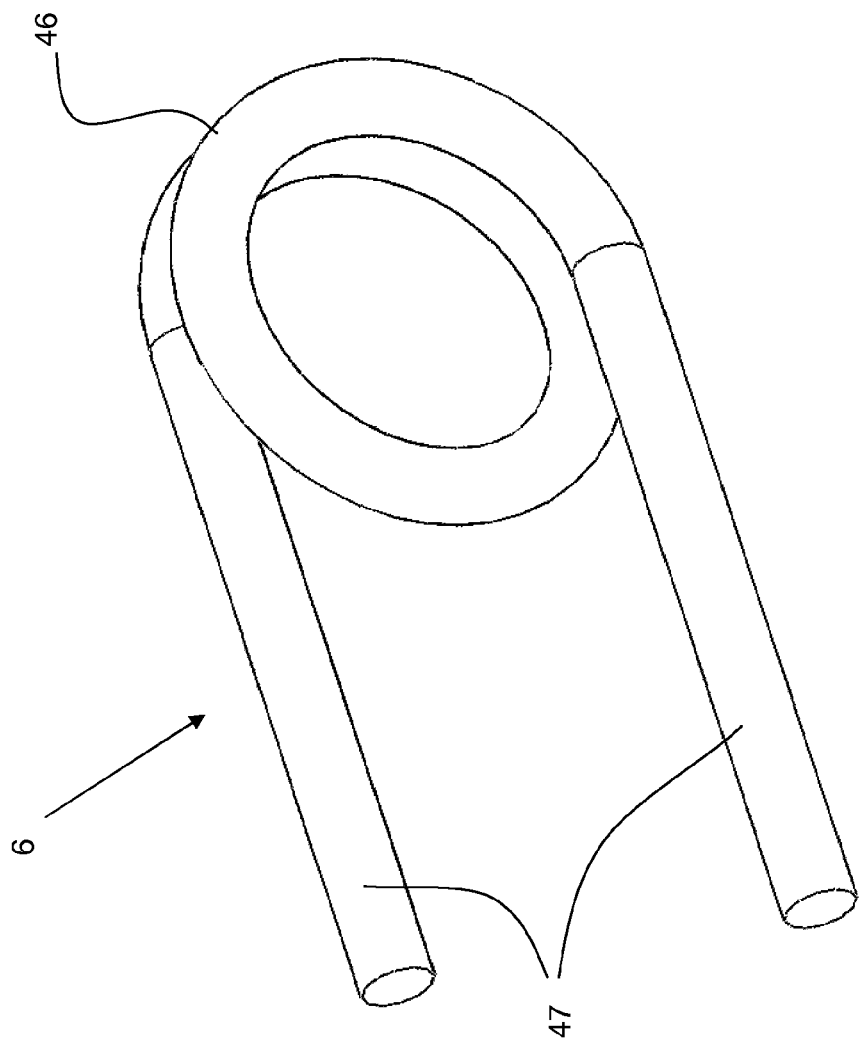
FIG. 19 depicts a perspective view of a return spring

FIG. 19 depicts a return spring 6 or staple folder having a double loop 46, keeping the spring within intended limits of elasticity. The legs 47 of the return spring 6 urge a staple folder block 10 back to a starting position.

FIG. 20 depicts a perspective view of staple mechanism housing 15 inserted into a handle 4, with the staple mechanism housing having one or more voids 48 sometimes used to view the quantity of remaining staples.

FIG. 21 depicts a perspective view of a sheath having grip tabs 2 shown in an open position wherein back edges are unsealed to allow for insertion of a handle assembly. Along the sealed perimeter, seam sections 3 are shown. The seam sections may be sealed with adhesive to allow the seams to be torn open for clean waste disposal of a handle assembly. The sheath is shown with a folded edge 60 having no seam. This folded edge 60 section is sometimes adhesively attached to a point or line upon a superior side 65 of a staple housing mechanism. An attachment point 19, (shown on FIG. 7) secures the folded edge 60 of the sheath with a superior side of a staple housing.

FIG. 22 depicts a side view of a handle assembly inserted into a sheath with a section of loose sheath 70 having a folded edge attached to a stapler mechanism housing by use of adhesive, heat seal, mechanical clip or other fastening methods.

FIG. 23 depicts a final assembly of a skin stapler or surgical stapler having a fully sealed sheath and inserted staple mechanism housing.

FIG. 24 depicts grip tabs in a pulled apart position, exposing portions of a handle assembly. FIG. 25 depicts a fully exposed handle assembly with a sheath pulling staple mechanism housing out of a handle assembly. FIG. 26 depicts a housing assembly separated from a staple mechanism housing.

Figure 27:
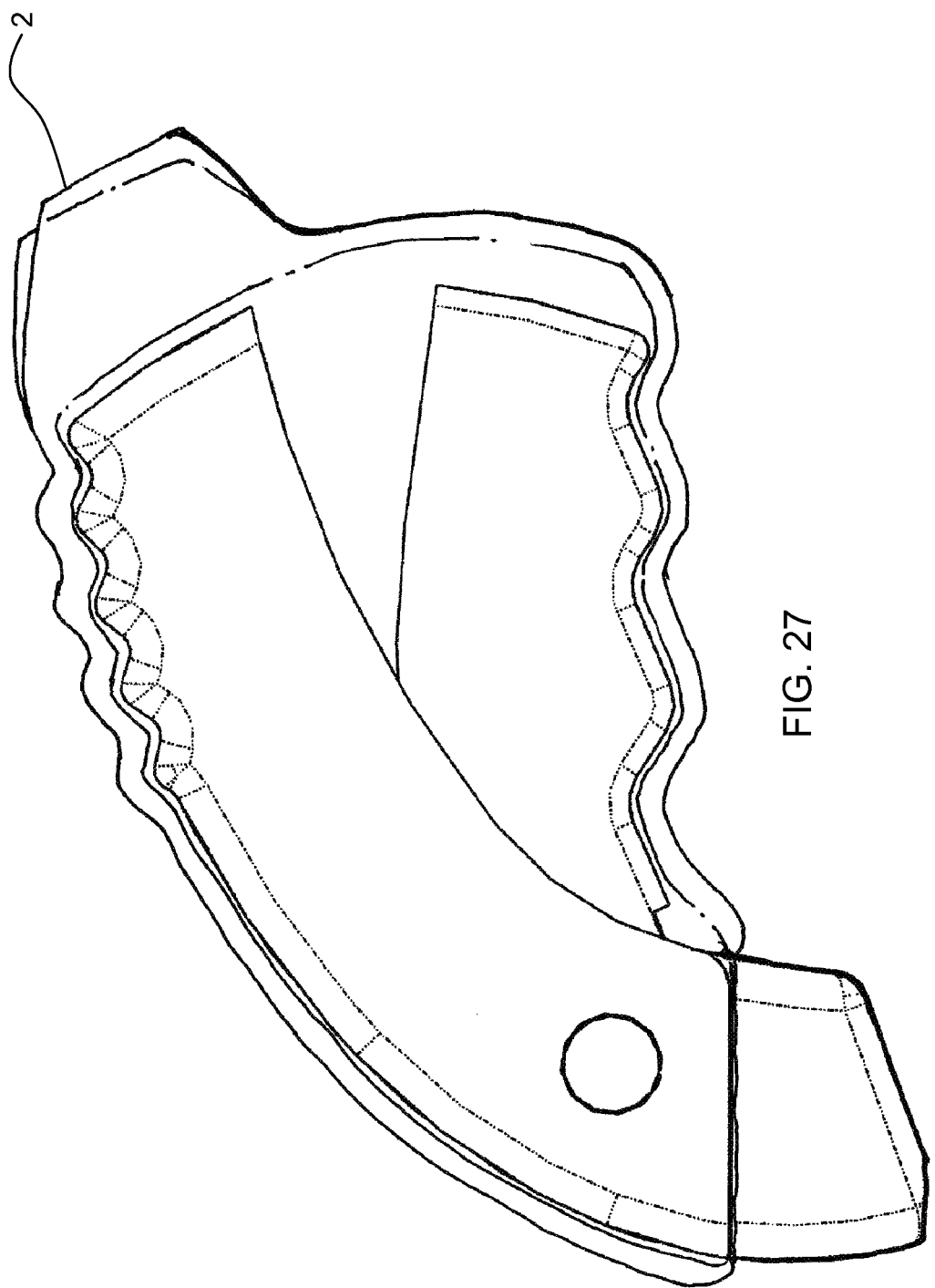
FIG. 27 depicts a surgical stapler with tabs for sheath removal

FIG. 27 depicts an assembled skin stapler or surgical stapler with a sealed sheath in place, the sheath having grip tabs.

Figure 28:
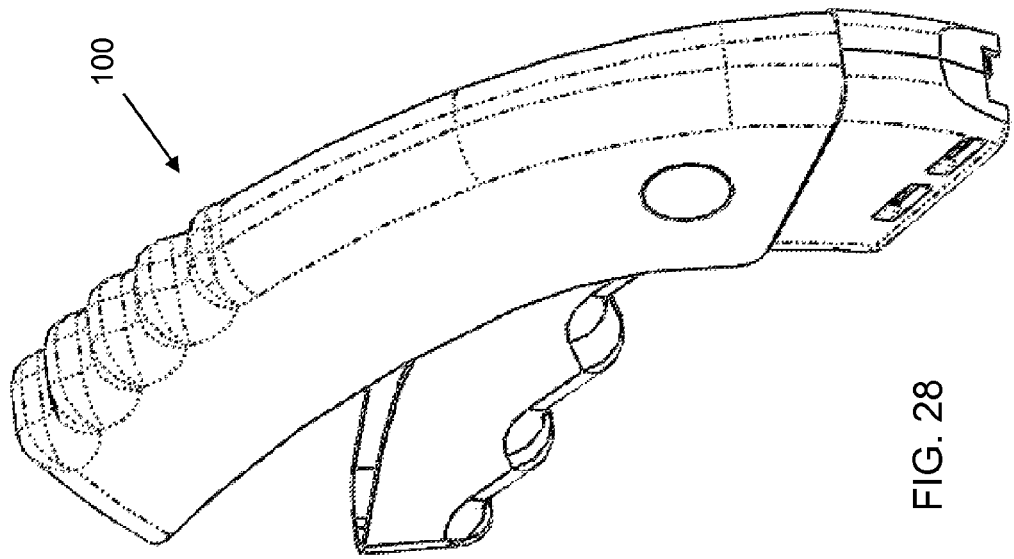
FIG. 28 depicts a surgical stapler in general

FIG. 28 depicts a skin stapler 100 in general, not having a sheath. The device is also sometimes referred to a surgical stapler.

Figure 29:
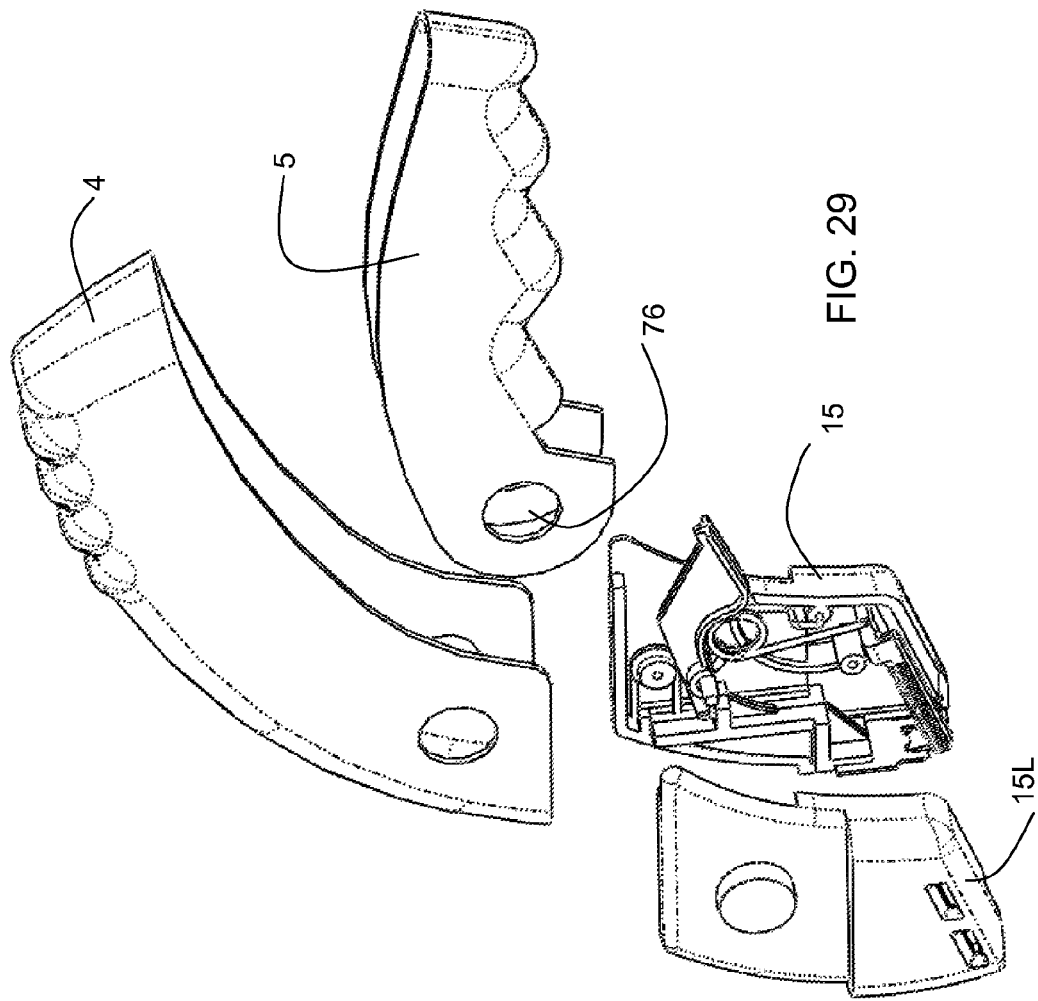
FIG. 29 depicts a surgical stapler components

FIG. 29 presents a handle 4, actuator grip lever 5 having a void 76 or center void sometimes used to mate with a boss 21. A left side 15L of staple mechanism housing is shown with a boss or actuator grip pivot. A right side 15R of staple mechanism housing is shown with a staple folder block, staple folder plate and metal staple carrier.

Items

Disclosed embodiments include the following items or descriptions.

Item 1. A surgical stapler system comprising:

a) a handle 4 having two center voids 75, an interior void 77 defined by exterior walls of the handle;

b) an actuator grip lever 5 having two center voids 76;

c) a staple mechanism housing 15 having one or more handle pivot bosses 16 fitted to fill the two center voids of 75 of the handle 4 and fitted to fill the two center voids 76 of the actuator grip lever 5, the staple mechanism housing 15 having a narrow section 66 attached to the bosses 16 and the narrow section fitted for insertion into the handle and actuator grip lever, the narrow section attached to a plurality of lateral ridges 67 and the plurality of lateral ridges attached to a base section 68, the base section fitted to not insert into either the handle 4 or actuator grip lever 5.

Item 2. The system of item 1 wherein the narrow section 66 of the staple mechanism housing 15 is further defined by a superior side 65, the superior side 65 in attachment to a sheath 1, the sheath having one or more seams 3 and one or more grip tabs 2.

Item 3. The system of item 2 wherein the sheath is comprised of a folded edge 60 attached to the superior side 65 of the staple mechanism housing 15, with the sheath further comprised of a loose section 70 configured to fit over the narrow section 66 and bosses 16.

Item 4. The system of item 3 wherein the loose section 70 of sheath covers the narrow section 66 and the bosses 16 when the narrow section is contained within the handle 4 and the bosses 16 extend though the center handle voids 75 and the center voids 77 of the actuator grip lever 5.

Item 5. The system of item 4 wherein the actuator grip lever 5 is in connection with a distal section 22 of an actuator lever 7, the actuator lever connected to the staple mechanism housing.

Item 6. The system of item 5 wherein the staple mechanism housing further comprises a right side component 15r and a left side component 15l, and the actuator lever 7 comprises one or more curved ribs 32, connected to a block area 34, wide rib 35 and one or more pivot pins 33, with a pivot pin 33 connected to a pivot void 31 defined by a side component 15r or 15l of the staple mechanism housing, the side component comprising a boss 24, a curved rib 25 a pivot void 26 a recess 27, a track 28, a front inside wall 29, and a vertical track 30.

Item 7. The system of item 6 wherein a return spring is attached to the boss 24, the curved rib 25 is connected to a staple advance spring 9, the pivot void is attached to the staple advance spring 9, the recess 27 holds a staple carrier tray 8, the track 28 holds a staple folder plate 11, the front inside wall 29 retains a staple, and the vertical track 30 retains a staple folder block 10.

Item 8. A method of protecting stapler components for clean bin recycling, the method comprising the steps of:
a) using a sheath 1 to cover a handle assembly 80, the handle assembly comprising a handle 4 and a actuator grip lever 5;
b) using a loose section 70 of the sheath to cover a narrow section 66 of a staple mechanism housing 15 and to cover one or more handle pivot bosses 16;
c) using a folded edge 60 of the sheath to attach to a superior side 65 of the staple mechanism housing;
d) sealing the sheath 1 along seams 3 and encasing the handle assembly 80;
d) using grip tabs 2 upon the sheath to pull the sheath from the handle assembly and releasing the handle assembly.

Item 9. The method of Item 8 including the step of using paper pulp material in the construction of the handle assembly.

Item 10. The method of item 9 including the step of dropping the handle assembly into a container, the container used for holding recyclable material.

Item 11. The method of claim 1 using lateral ledges 67 upon the staple housing mechanism 15 as stopping block to stop the further insertion of the staple housing mechanism into the handle assembly.

Item 12. A surgical stapler kit comprising:
a) a handle assembly 80 comprising a handle 4 and a actuator grip lever 5;
b) a sheath 1 comprising seams 3, grip tabs 2 and a folded edge 60; and
c) a staple mechanism housing 15 comprising a narrow section 66, a superior side 65, lateral ledges 67 and a base section 68.

Item 13. The kit of item 12 wherein the staple mechanism housing further comprises a right side 15R component and a left side 15L component, with each side component comprising a boss 24, a curved rib 25, a pivot void 26, a recess 27, a track 28, a front inside wall 29 and a vertical track 30.

Item 14. The kit of item 13 further comprising a return spring 6, an actuator lever 7, a staple carrier tray 8, a staple advance spring 9, a staple folder block 10, a staple folder plate 11, a staple stack 12, and a staple advance block 13.

Item 15. The kit of item 14 wherein the actuator lever 7 is comprised of a distal section 22, on or more curved ribs 32, a block contact area 34, a wide rib 35 and one or more pivot pins 33.

Item 16. The kit of item 14 wherein the staple folder block comprises one or more vertical ribs 38, one or more curved ribs 38, a protruding surface 37, a recessed area 39 with the recessed area including a raised block 40.

Item 17. The kit of item 14 wherein the staple advance spring 9 is comprised of a pivot leg 41, an offset 42, a plurality of loops 43, a pusher leg 44 and a leg 45.

Item 18. The kit of item 14 wherein the return spring 6 comprises a plurality of loops 46 and two legs 47.

Item 19. The kit of item 14 wherein the base section 68 of the staple mechanism housing 15 includes a viewing void 48, FIG. 20.

Item 20. The kit of item 14 wherein the sheath is transparent.

What is claimed is:

1. A surgical stapler system comprising:
a) a handle having two center voids defined by exterior walls of the handle;
b) an actuator grip lever having two center voids;
c) a staple mechanism housing having one or more handle pivot bosses fitted to fill the two center voids of the handle and fitted to fill the two center voids of the actuator grip lever, the staple mechanism housing having a narrow section attached to the bosses and the narrow section fitted for insertion into the handle and actuator grip lever, the narrow section attached to a plurality of lateral ridges and the plurality of lateral ridges attached to a base section, the base section fitted to not insert into either the handle or actuator grip lever.

2. The system of claim 1 wherein the narrow section of the staple mechanism housing is further defined by a superior side, the superior side in attachment to a sheath, the sheath having one or more seams and one or more grip tabs.

3. The system of claim 2 wherein the sheath is comprised of a folded edge attached to the superior side of the staple mechanism housing, with the sheath further comprised of a loose section configured to fit over the narrow section and the bosses.

4. The system of claim 3 wherein the loose section of sheath covers the narrow section and the bosses when the narrow section is contained within the handle and the bosses extend though the center handle voids and the center voids of the actuator grip lever.

5. The system of claim 4 wherein the actuator grip lever is in connection with a distal section of an actuator lever, the actuator lever connected to the staple mechanism housing.

6. The system of claim 5 wherein the staple mechanism housing further comprises a right side component and a left side component, and the actuator lever comprises one or more curved ribs, connected to a block area, wide rib and one or more pivot pins, with a pivot pin connected to a pivot void defined by a side component of the staple mechanism housing, the side component comprising a boss, a curved rib, a pivot void, a recess, a track, a front inside wall and a vertical track.

7. The system of claim 6 wherein a return spring is attached to the boss, the curved rib is connected to a staple advance spring, the pivot void is attached to the staple advance spring, the recess holds a staple carrier tray, the track holds a staple folder plate, the front inside wall retains a staple, and the vertical track retains a staple folder block.

8. A surgical stapler kit comprising:
a) a handle assembly comprising a handle and an actuator grip lever;
b) a sheath comprising seams, grip tabs and a folded edge; and
c) a staple mechanism housing comprising a narrow section, a superior side, lateral ledges and a base section.

9. The kit of claim 8 wherein the staple mechanism housing further comprises a right side component and a left side component, with each side component comprising a boss, a curved rib, a pivot void, a recess, a track, a front inside wall and a vertical track.

10. The kit of claim 9 further comprising a return spring, an actuator lever, a staple carrier tray, a staple advance spring, a staple folder block, a staple folder plate, a staple stack and a staple advance block.

11. The kit of claim 10 wherein the actuator lever is comprised of a distal section, one or more curved ribs, a block contact area, a wide rib and one or more pivot pins.

12. The kit of claim 10 wherein the staple folder block comprises one or more vertical ribs, one or more curved ribs, a protruding surface, a recessed area with the recessed area including a raised block.

13. The kit of claim 10 wherein the staple advance spring is comprised of a pivot leg, an offset, a plurality of loops, a pusher leg and a leg.

14. The kit of claim 10 wherein the return spring comprises a plurality of loops and two legs.

15. The kit of claim 10 wherein the base section of the staple mechanism housing includes a viewing void.

16. The kit of claim 10 wherein the sheath is transparent.

* * * * *